Figure 1:
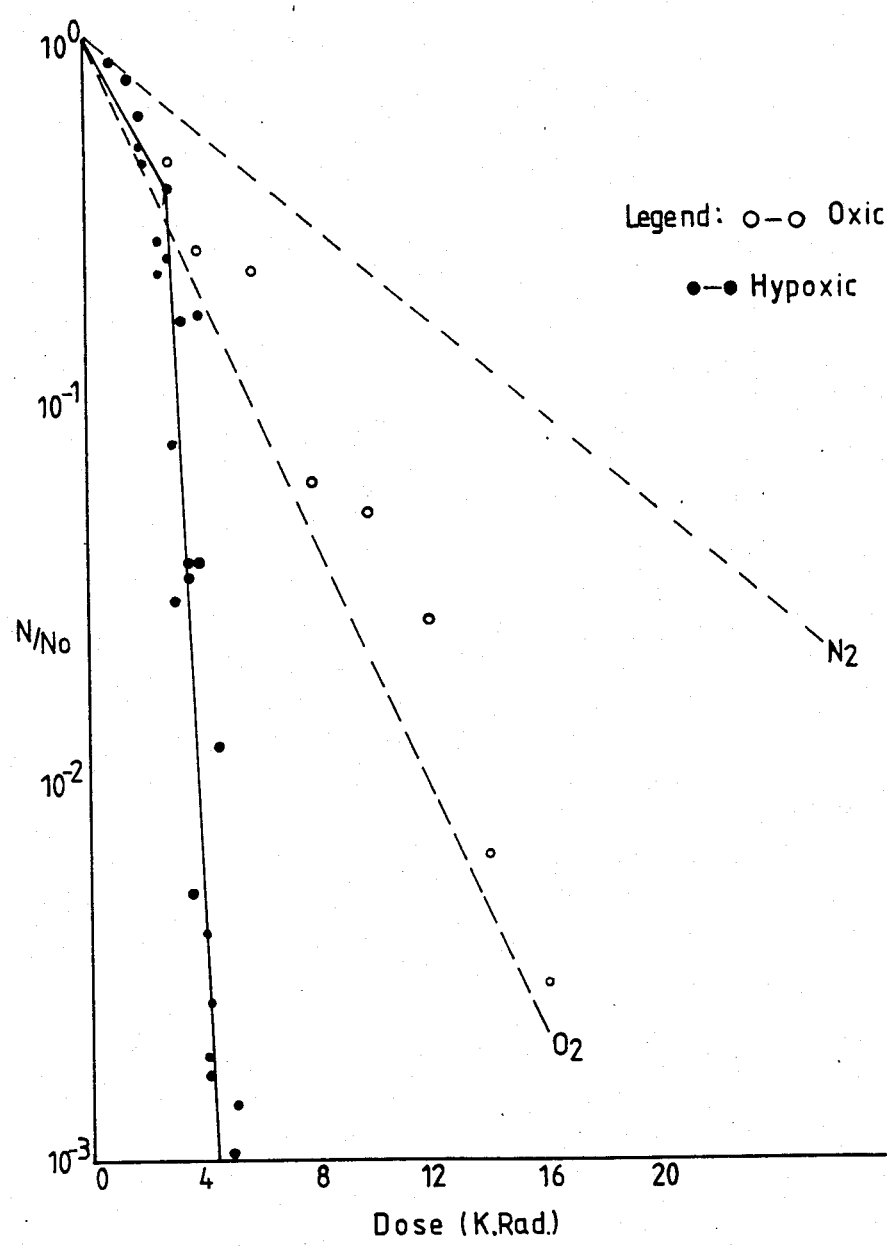

United States Patent [19]

Picker et al.

[11] Patent Number: 4,681,091
[45] Date of Patent: Jul. 21, 1987

[54] COMBINATION MODALITY CANCER THERAPY

[76] Inventors: Donald H. Picker, 310 Woodside Ave., Narberth, Pa. 19380; Paul C. Hydes, 13 Woodlands Grove, Caversham, Reading, Berkshire, RG4 ONB, United Kingdom

[21] Appl. No.: 802,232

[22] Filed: Nov. 27, 1985

Related U.S. Application Data

[63] Continuation-in-part of Ser. No. 637,556, Aug. 3, 1984, abandoned.

[51] Int. Cl.$^4$ ............................................. A61B 19/00
[52] U.S. Cl. ..................................... 128/1 R; 424/1.1
[58] Field of Search ................... 128/1 R, 1.1, 1.3, 1.5; 424/1, 1.1

[56] References Cited

U.S. PATENT DOCUMENTS

| | | | |
|---|---|---|---|
| 4,303,636 | 12/1981 | Gordon | 128/1.1 |
| 4,452,774 | 6/1984 | Jones et al. | 260/464 |

OTHER PUBLICATIONS

Chibber et al, "Radiosensitization of Mammalian Cells by Transition Metal Complexes Containing Nitroimidazole Ligands" J. Radiat. Oncol Biol. Phys. U.S.A., 1984, pp. 1213-1215.

*Primary Examiner*—John D. Yasko
*Attorney, Agent, or Firm*—Cushman, Darby & Cushman

[57] ABSTRACT

Coordination compounds for use in therapy, the compounds having the general empirical formula $$[Rh^m X_x Y_y]^a$$

in which m is the oxidation state of Rh, X is at least one anionic ligand, Y is at least one neutral ligand, with the proviso that at least one of X and Y is a nitrogen donor ligand, x is an integer from 1 to 6, y is an integer from 1 to 5 or may be equal to zero, and a is a positive or negative integer from $-3$ to $+3$ or may be equal to zero.

Such compounds are useful inter alia as radiosensitizers in the treatment of cancer. A preferred compound is [RhenCl$_4$][enH$_2$].

4 Claims, 3 Drawing Figures

COMBINATION MODALITY CANCER THERAPY

This application is a continuation in part of Ser. No. 637,556 filed Aug. 3, 1984, now abandoned.

This invention relates to compounds for use in therapy, particularly in combination modality cancer therapy with other forms of treatment.

One established form of cancer treatment is irradiation by high-energy particles or electromagnetic waves, typically electrons, X-rays or gamma rays, generally referred to as ionising radiation. Part of the difficulty associated with this form of treatment, however, is the response of different target cells to the radiation. Whereas well oxygenated ("oxic") cells are susceptible to the cell-killing effects of the irradiation, oxygen-deficient ("hypoxic") cells are more resistant. In a solid tumour, particularly a rapidly-growing one, there are, in terms of oxygen content, three types of cell. Those cells farthest from the blood supply, and hence those most oxygen-deficient, are or may be already necrotised from oxygen starvation; those closest to the blood supply are oxic and are therefore actively dividing whereas those in between are hypoxic and in a dormant state. After conventional irradiation treatment, which is particularly effective against the oxic cells, the destruction of these oxic cells enables oxygen to penetrate to some of the hypoxic cells which therefore become reoxygenated. However, any radioresistant hypoxic cells which survive have the potential to divide and thus they may either initiate regrowth of the primary tumour or migrate to set up metastases. Failure to sterilize these hypoxic tumour cells may explain why radiation therapy is not always successful whereas radiosensitization of these hypoxic cells may result in an improved efficiency for radiation in the treatment of cancer.

We have now found that certain coordination compounds of rhodium are useful in combination modality therapy with existing methods of treatment of cancer.

According to the invention, therefore, we provide coordination compounds for use in therapy, the compounds having the general empirical formula $$[Rh^m X_x Y_y]^a \quad (I)$$

in which m is the oxidation state of Rh, X is at least one anionic ligand, Y is at least one neutral ligand, with the proviso that at least one of X and Y is a nitrogen donor ligand, x is an integer from 1 to 6, y is an integer from 1 to 5 or may be equal to zero, and a is a positive or negative integer from $-3$ to $+3$ or may be equal to zero.

The oxidation state of rhodium is preferably III but may be II.

A nitrogen donor ligand is an ion or molecule which donates electrons to the coordinate bond via a nitrogen atom. Nitrogen donor ligands may be monodentate or polydentate. Suitable nitrogen donor ligands include ammine, amines, bi-, di- or tetra-functional amines such as ethylenediamine and substituted derivatives thereof, nitrosyl and nitro groups and nitrogen heterocycles.

The anionic ligand X may be selected from ligands such as nitrite, halogen, hydroxy, azide, thiocyanate, formate, acetate, chloroacetate, carbonate, oxalate, malonate, sulphate, thiosulphate and aminoacid. The neutral ligand Y may be selected from monodentate ligands such as ammine ($NH_3$), pyridine and water and bidentate ligands such as ethylenediamine, ethylenediaminetetraacetic acid and dimethylglyoxime.

Where a is negative, the compound includes a complex anion and the counter ion may be selected from ammonium, sodium, potassium and the like. Where a is positive, the compound includes a complex cation and the counter ion may be selected from halide, sulphate, and other anions.

Examples of compounds according to the invention include the following:

| | |
|---|---|
| $[RhenCl_4]^-$ | (en = ethylenediamine: counter-ion is $[enH_2]^{2+}$) |
| $K_3Rh(NO_2)_6$ | |
| cis $[RhCl_2en_2]Cl$ | |
| $[RhCl_3(NH_3)_3]$ | |
| $KIr(NO)Br_5$ | |
| $[RhCl(NH_3)_5]Cl_2$ | |
| $K_2Pt(NO_2)_4$ | |
| $K_2Pd(NO_2)_4$ | |
| $[RhCl(NH_3)_5]SO_4$ | |
| $K[Rh(NO_2)_4(NH_3)_2]$ | |
| $[Rh(NO_2)_3L_3]$ | (L = $NH_3$ or pyridine) |
| $Rh(NO_2)_2(en)_2]NO_3$ | |
| $NH_4[Rh(DMG)_2(NO_2)_2]$ | (DMG = dimethylglyoxime) |
| $[Rh_2(NH_3)_2(N_2)(NO_2)_6(OH)_2]^2$ | |
| $[Rh(NO_2)(NH_3)_5]Cl_2$ | |
| $[Rh(NO_2)_5(H_2O)]^{2-}$ | |
| $[Rh(NO_2)_4(H_2O)_2]^-$ | |
| $K_3[Rh(NO_2)_3Cl_3]$ | |
| $K_2[Rh(NO_2)_3(H_2O)(SO_4)]$ | |
| $K_2[Rh_2X_4(NO_2)_2]$ | |
| $K_3[Rh(EDTA)(NO_2)(OH)]$ | |
| $[Rh(en)_2X_2]^+$ | (X = Br, I, SCN, $N_3$, OH, acetate<br>$X_2$ = carbonate, oxalate, malonate) |
| $[Rh(en)_2X]^{2+}$ | (X = amino acid) |
| $[Rh(en)_2ClX]^+$ | |

The above compounds are known per se and their preparation is documented in the chemical literature. For example, the preparation of $[RhenCl_4]_2[enH_2]$ may be found in Inorganic Chemistry, 1962, 1, 925 (F. A. Johnson and F. Basolo) the contents of which are herein incorporated by reference.

We believe that compounds according to the invention are effective in combined modality therapy with existing methods for the treatment of cancer, in particular ionising irradiation by rendering hypoxic cells more sensitive to irradiation. Not all compounds which show a beneficial effect in rendering hypoxic cells more sensitive to irradiation, or in combination with other existing methods of treatment, are necessarily capable of showing benefits to humans in the clinic, however, since they may be either per se toxic or may provide radiation-induced or other acquired degradation products which are toxic to healthy cells—that is, normal living tissue—as well as to tumour cells. The invention therefore particularly provides coordination compounds which, despite any inherent toxicity or acquired toxicity, show a net beneficial anti-tumour effect in combination with existing methods of treatment.

The invention also provides a pharmaceutical composition comprising an effective amount of a coordination compound according to general formula (I) in association with a pharmaceutically-acceptable carrier, diluent or excipient therefor. Furthermore, the invention includes the use of a compound according to general formula (I) in the treatment of cancer, and a method for the treatment of cancer in a human or non-human animal body comprising administering to said body an effective amount of a coordination compound according to general formula (I) in combination with treatment by ionising irradiation. Preferably the said compound is administered before irradiation.

Compounds according to the invention are evaluated in toxicity and radio-sensitisation screens in bacterial cells, in cultured rodent and human cells and in human and animal tumours implanted in mice. The toxicity screen is used to evaluate the cytotoxicity of the compound itself and its irradiation products. The method of testing in bacterial cells is as follows.

Bacterial cells (salmonella typhimurium TM677) in phosphate buffered saline (PBS) are exposed at room temperature (ca. 25° C.) to each compound at 200 $\mu$M concentration. At an appropriate time interval, a sample of mixture is removed and diluted 1:100 in PBS before the cells are plated out in petri dishes. After allowing a period for growth, bacterial colonies are counted to determine the number of surviving cells. The ratio of this number of the number of cells in a control sample is then plotted against time of exposure to yield the toxicity curve.

This experiment may be repeated at a lower concentration of compound or at 0° C. if a high level of toxicity is seen at 200 $\mu$M.

In addition to the above protocol, each compound which shows radiosensitisation (method for radiosensitization testing described later) is made up at 210 $\mu$M in PBS and irradiated to 17 krad of x-irradiation. This is done under both oxygenated and de-oxygenated conditions (the latter is achieved by degassing using a nitrogen stream for ca. 10 min). The solution is diluted to 200 $\mu$M with bacterial suspension, and the mixture is then treated as before to obtain a toxicity curve for these irradiated solutions. In all cases the period of bacterial exposure to the compounds is carried out under oxygenated conditions.

Comparison of the toxicity curves for these three different experiments allows the existence of radiation-induced toxic products to be established.

The radiosensitisation experiment is carried out as follows. The bacterial cells are suspended in PBS in the irradiation vessel and the compound is added to achieve a concentration of 200 $\mu$M (or a lower value if the compound is highly toxic). The cells may be made hypoxic by passing a stream of nitrogen through the suspension for 10–15 mins. The initial dose of X-irradiation is then given (up to 4 krad at 4 krad/min). A sample of the suspension is then taken and added to PBS to achieve a 1:100 dilution. A further 1:10 dilution is performed before plating out. The addition of growth medium at this stage may involve a further 1:10 up to 1:1000 dilution giving an overall dilution factor from the irradiated solution of $10^4$–$10^6$. Additional doses of irradiation (ca. 4 krad each) are given up to a total of ca. 20 krad with samples being taken after each dose. Cell survival is then determined as previously described and the surviving fraction is plotted versus the dose of radiation. Baseline curves for irradiation of the bacteria under oxic and hypoxic conditions in the absence of the compound are also determined to allow a quantitative estimation of the efficiency of the compound in sensitising the cells to radiation-induced killing. This quantification may be expressed in the form of an enhancement ratio calculated from the slope of the survival curve in the presence of the compound divided by the slope of the survival curve in the absence of the compound.

The method of testing in mammalian cells is as follows:

In vitro

Confluent, plateau-phase monolayers of rodent cells (V79 and CHO) or human fetal lung fibroblasts (HFL) which have been growing for 7 days are treated with the test compounds for two hours. Immediately after addition of the drug to the culture media, the petri dishes containing the cells are placed into aluminium chambers which are then degassed and purged with nitrogen to produce hypoxia. The degassing/back-filling cycle is repeated two times and the cells are irradiated with cobalt-60 gamma rays in the aluminium chambers at the end of the two hours. Control, un-irradiated cell cultures are exposed to the drug in various concentrations to assess drug cytotoxicity. Immediately following irradiation the cells are removed from the petri dishes using trypsin enzyme for 6 minutes, pipetted into single cell suspensions, and serially diluted for subculturing in triplicate petri dishes containing 5 cc of fresh culture media without the test compound. These dishes are incubated in 5% $CO_2$ at 37° C. for 10 days and, following staining, the colonies are counted to produce survival curves (surviving fraction of cells versus compound concentration or radiation dose). As in the bacterial radiosensitization tests, baseline curves for irradiation of the mammalian cells under oxic and hypoxic conditions in the absence of the compound are also determined to allow a quantitative estimation of the efficiency of the compound in sensitizing the cells to radiation-induced killing by deriving enhancement ratios. Test results in oxic cells irradiated in air in the presence of the compounds are compared to the hypoxic tests to confirm that the effect is specifically hypoxic cell radiosensitization.

In vivo

In order to test if the compounds will produce radiosensitization of human tumour cells under physiological conditions approaching clinical cancer environments, the compounds are injected i.p. into immune-suppressed or nude mice bearing human malignant melanoma tumours (HX-34). These tumours of approximately 1 cm diameter are grown from cells which are injected into the hind legs of the mice approximately 3 weeks prior to treatment. Results of initial toxicity tests in non-tumoured mice are used to estimate the maximum tolerated dose of compounds which will not produce significant percentage lethality and this level of compound is used in the radiosensitization tests. One hour following injection of the compound the tumour cells are irradiated in situ with a whole-body dose of cobalt-60 gamma rays of 12.5 Gy. The mice are sacrificed and tumours are removed and minced to disperse tumour cells. The cells are separated into single cell suspensions using an enzyme cocktail for 30 minutes. The cells are counted, serially diluted, and placed into agar suspensions in plastic test tubes. These agar suspensions are incubated in 5% $O_2$/ 5% $CO_2$ and 80% nitrogen for three weeks. At the end of this period the agar suspension is placed on a slide and colonies are counted to quantify tumour cell survival. The surviving fraction of tumour cells in mice which received irradiation following injection of the compound is compared to the surviving fraction obtained from tumour cells which received either radiation or the compound alone.

In summary, these tests in mammalian cells (V79, CHO, HFL) and in human tumour xenografts (HX-34) enable the radiosensitization effects observed in the bacterial screens to be extended to models of human cancer. These cell and tumour systems are standard cancer research methods which have been used in the past to assess the efficacy of other classes of chemical radiosensitizers and should serve as appropriate predictors of the effectiveness of these test compounds in improving the radiation therapeutic effects in human cancer.

Experimental results for toxicity of test compounds, radiation-induced toxicity and radiosensitisation, all in relation to bacterial cells, are presented for various compounds by way of example.

In Table 1 below, results for radiosensitisation are quoted according to averages obtained over several experiments. Under hypoxic conditions, compounds which give the best a radiosensitisation effect whereby there is no cell survival following irradiation at up to 8 krad are indicated by "B", while those giving a more modest but nevertheless significant effect at up to 16 krad, in that the cells are rendered more susceptible to the irradiation than untreated cells under oxic conditions, are indicated by "C".

Under oxic conditions, cells are reasonably susceptible to irradiation without requiring sensitisation. Nevertheless, in Table 1, those compounds which in addition to showing a sensitisation effect under hypoxic conditions also show a slight or moderate effect under oxic conditions are indicated by "D" whereas those compounds which show no sensitisation under oxic conditions are indicated by "E". None of the compounds in the Table was toxic to bacterial cells, either in the absence of or following irradiation at 17 krad.

In contrast to the above, compounds such as rhodium trichloride, rhodium acetate, rhodium nitrate, tetra-n-butylammoniumdicarbonyldichlororhodium (I) and rhodium oxide were either too toxic, not soluble in water or failed altogether to show a sensitisation effect.

The detailed results for two of the compounds from Table 1 (nos. 2 and 3) are shown in Tables 2 to 7 below and illustrated in accompanying FIGS. 1 and 2.

In Tables 2 to 7, Tables 2 to 4 relate to compound no. 2 (potassium hexanitrorhodium (III)—$K_3[Rh(NO_2)_6]$) and Tables 5 to 7 relate to compound no. 3 (dichlorobis (ethylenediamine) rhodium (III)—cis[$Rh(en)_2Cl_2$]Cl). Tables 2 and 5 show results for toxicity of the compounds themselves and of their irradiated products under oxygenerated and de-oxygenated conditions. Tables 3 and 6 show results for sensitisation under hypoxic conditions and Tables 4 and 7 show results for sensitisation under oxic conditions. In each Table, the ratio N/No which appears in the final column is the figure for the average colony count at various times t divided by the average colony count at time t=0, adjusted for any aliquot dilution, and is an indication of the toxicity or sensitisation, as the case may be.

Figure 2:
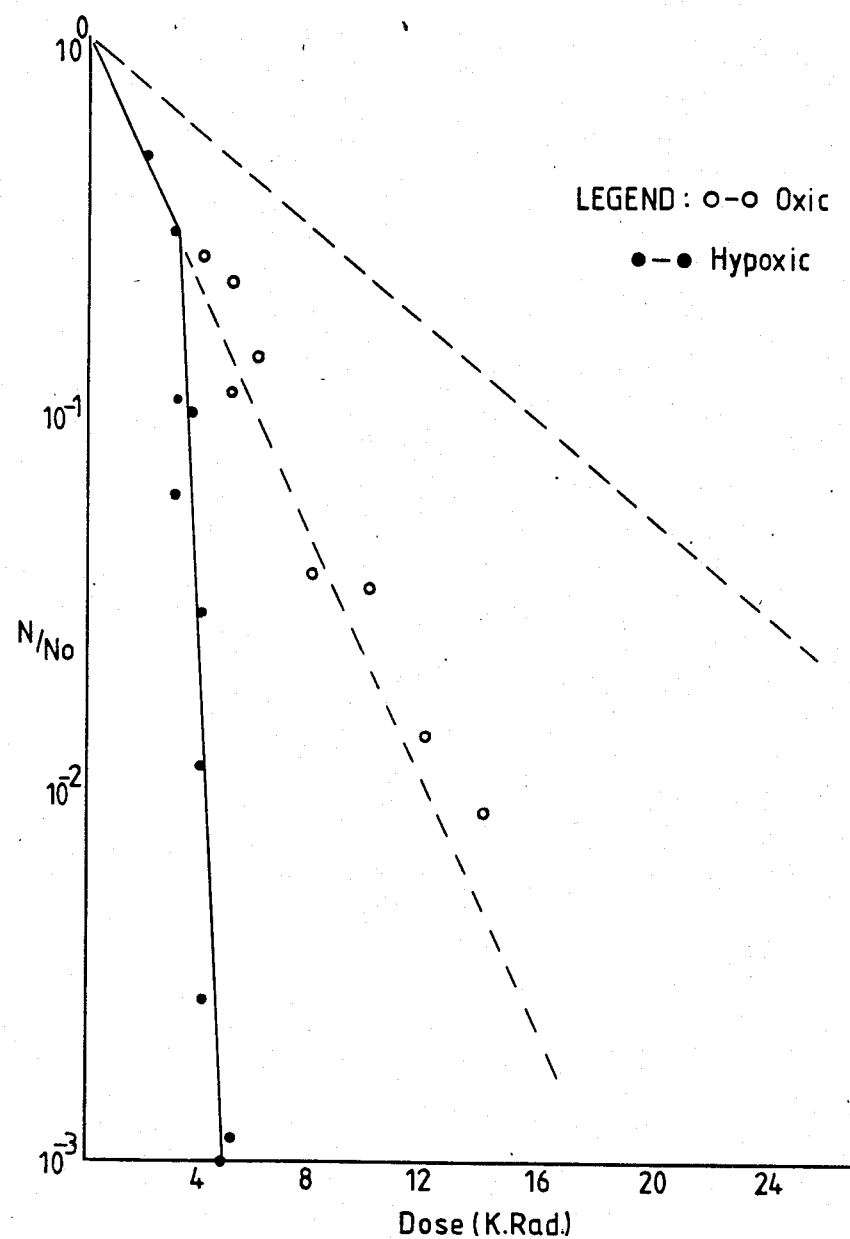

Accompanying FIGS. 1 and 2 illustrate graphically the sensitisation of compounds 2 and 3. In the figures, the dotted lines illustrate the effect of irradiation on untreated bacterial cells, that is, in the absence of a sensitisation compound, under oxic (indicated by $O_2$) and hypoxic conditions (indicated by $N_2$). The legend for the plotted points is given on the Figures. The dramatic improvement for cell-kill (N/No) as between unsensitised cells and sensitised cells under hypoxic conditions is immediately apparent.

Figure 3:
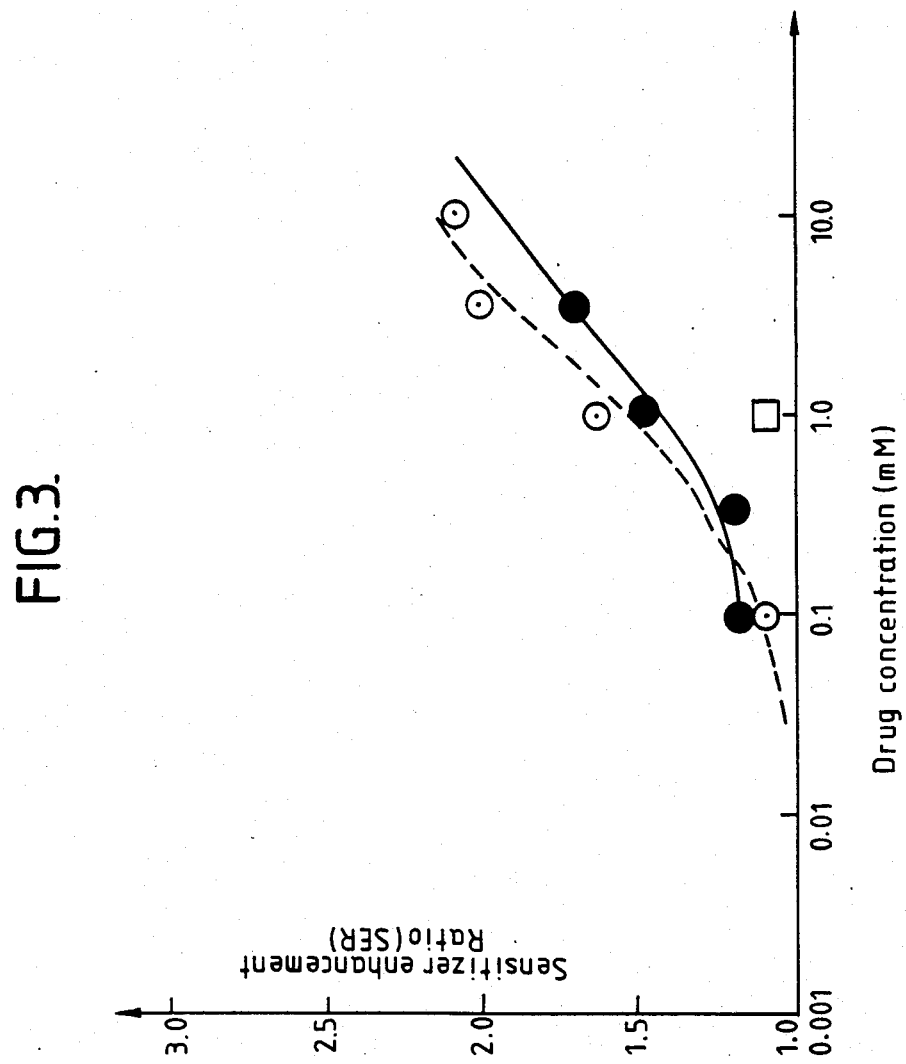

FIG. 3 is a graph showing cytotoxicity and hypoxic radiosensitization for compound [$RhenCl_4]_2[enH_2$.] Radiosensitization results are in vitro in mammalian cell culture, compared with misonidazole as control. Misonidazole is a "standard" radiosensitization drug which has been discussed in the literature inter alia in "Int. J. Radiation Oncology Biol. Phys.", Vol. 10, pp 425–429 (1984).

In FIG. 3, the dotted line represents the standard or average reported misonidazole response. The symbols " " and ' ' represent experimental misonidazole response and the experimental Rh compound response respectively.

It will therefore be seen that the compound according to the invention has an activity approaching the activity of misonidazole, and in particular the concentration required to give an ser (sensitizer enhancement ratio) of 1.6 is 2.0 mM compared with 1.5 mM for misonidazole, i.e. 75% effectiveness compared with misonidazole.

The symbol "□" in FIG. 3 represents the aerobic (oxic) response, which is effectively zero.

Experimental and process details used when carrying out the radiosensitization and cytotoxicity tests of the compound [$RhenCl_4]_2[enH_2$] were as follows:

Solubility 20 - 100 mM.
1 hour hypoxic cytotoxicity:
0.033 mM %: 0.1 mM 95%: 0.33 mM 83.6%: 1.0 mM 62.7%
3.3 mM 22% 10.0 <1%.
1 hour Aeroboc Cytotoxicity
0.1 mM 78.0%: 1 mM 61.0% 10 mM 6.1%.
Hypoxic Radiosensitization:
$C_{1.6}$(drug) 2.0 mM $C_{1.6}$(MISO) 1.5 mM.

TABLE 1

| No. | Compound | Sensitisation Hypoxic | Sensitisation Oxic |
|---|---|---|---|
| 1 | $Rh(NH_3)_3Cl_3$ | B | D |
| 2 | $K_3[Rh(NO_2)_6]$ | B | E |
| 3 | $[Rh(en)_2Cl_2]Cl$ | B | E |
| 4 | $[RhCl(NH_3)_5]SO_4$ | C | D |

TABLE 2

Toxicity of compound 2

| Conditions | t (min) | Aliquot dilution | Colony counts | | | Average count | N/No |
|---|---|---|---|---|---|---|---|
| No x-ray | 0 | $10°$ | 71 | 61 | 66 | 66 | 1 |
|  | 30 | $10°$ | 57 | 80 | 71 | 69 | $1.05 \times 10°$ |
|  | 60 | $2 \times 10°$ | 120 | 133 | 123 | 125 | $9.49 \times 10^{-1}$ |
|  | 90 | $10°$ | 70 | 70 | 63 | 68 | $1.02 \times 10°$ |
| $N_2$ + x-ray | 0 | $10°$ | 61 | 56 | 56 | 58 | 1 |
|  | 30 | $10°$ | 52 | 62 | 59 | 58 | $1.0 \times 10°$ |
|  | 60 | $2 \times 10°$ | 81 | 99 | 82 | 87 | $7.53 \times 10^{-1}$ |
|  | 90 | $10°$ | 58 | 44 | 42 | 48 | $8.28 \times 10^{-1}$ |
|  |  | $5 \times 10°$ | 186 | 174 | 171 | 177 | $6.10 \times 10^{-1}$ |

TABLE 2-continued

Toxicity of compound 2

| Conditions | t (min) | Aliquot dilution | Colony counts | | | Average count | N/No |
|---|---|---|---|---|---|---|---|
| $O_2$ + x-ray | 0 | $10^\circ$ | 62 | 72 | 60 | 65 | 1 |
| | 30 | $10^\circ$ | 75 | 69 | 63 | 69 | $1.06 \times 10^\circ$ |
| | 60 | $10^\circ$ | 69 | 80 | 74 | 74 | $1.14 \times 10^\circ$ |
| | 90 | $10^\circ$ | 79 | 59 | 55 | 64 | $9.90 \times 10^{-1}$ |

TABLE 3

X-ray sensitisation of compound 2 under hypoxic conditions

| Dose | Dilution | Colony counts | | | Average Count | N/No |
|---|---|---|---|---|---|---|
| 0 | $10^\circ$ | 41 | 47 | 48 | 45 | 1 |
| 4 | $2 \times 10^\circ$ | 8 | 16 | 21 | 15 | $1.67 \times 10^{-1}$ |
| 6 | $10^\circ$ | 0 | 0 | 0 | | |
| 10 | $5 \times 10$ | 0 | 0 | 0 | | |
| 0 | $10^\circ$ | 81 | 86 | 74 | 80 | 1 |
| 2 | $2 \times 10^\circ$ | 81 | 78 | 72 | 77 | $4.81 \times 10^{-1}$ |
| 5 | $5 \times 10^1$ | 3 | 4 | 1 | 3 | $6.7 \times 10^{-4}$* |
| 8 | $2 \times 10^2$ | 0 | 2 | 0 | 1 | $4 \times 10^{-5}$* |
| 10 | $1 \times 10^3$ | 5 | 2 | 1 | 3 | $3.7 \times 10^{-5}$* |
| 0 | $10^\circ$ | 58 | 57 | 51 | 55 | 1 |
| 1 | $10^\circ$ | 53 | 48 | 45 | 49 | $8.85 \times 10^{-1}$ |
| 2 | $2 \times 10^\circ$ | 49 | 59 | 61 | 56 | $5.12 \times 10^{-1}$ |
| 3 | $5 \times 10^\circ$ | 19 | 29 | 21 | 23 | $8.36 \times 10^{-2}$ |
| 4 | $5 \times 10^\circ$ | 0 | 0 | 0 | | |
| 5 | $5 \times 10^2$ | 31 | 24 | 30 | 18 | $1.03 \times 10^{-3}$ |
| 6 | $1 \times 10^3$ | 19 | 27 | 28 | 25 | $4.48 \times 10^{-4}$ |
| 0 | $10^\circ$ | 54 | 62 | 83 | 66 | 1 |
| 3 | $2 \times 10^\circ$ | 62 | 47 | 52 | 54 | $4.06 \times 10^{-1}$ |
| 3.5 | $2 \times 10^1$ | 147 | 157 | 155 | 153 | $1.16 \times 10^{-1}$ |
| 4 | $2 \times 10^1$ | 27 | 79 | 53 | 53 | $4.02 \times 10^{-2}$ |
| 4.5 | $10^2$ | 81 | 90 | 83 | 85 | $1.28 \times 10^{-2}$ |
| 5 | $1 \times 10^3$ | 104 | 95 | 97 | 99 | $1.41 \times 10^{-3}$ |

*Estimate based on low colony counts.

TABLE 4

X-ray sensitisation of compound 2 under oxic conditions

| Dose | Dilution | Colony counts | | | Average Count | N/No |
|---|---|---|---|---|---|---|
| 0 | $10^\circ$ | 62 | 84 | 82 | 76 | 1 |
| 4 | $5 \times 10^\circ$ | 110 | 93 | 100 | 101 | $2.66 \times 10^{-1}$ |
| 6 | $10^1$ | 111 | 113 | 112 | 112 | $1.47 \times 10^{-1}$ |
| 10 | $5 \times 10^1$ | 132 | 134 | 134 | 133 | $3.51 \times 10^{-2}$ |
| 14 | $2 \times 10^2$ | 143 | 130 | 134 | 136 | $8.92 \times 10^{-3}$ |
| 0 | $10^\circ$ | 85 | 110 | 106 | 101 | 1 |
| 5 | $5 \times 10^\circ$ | 124 | 107 | 114 | 115 | $2.28 \times 10^{-1}$ |
| 8 | $2 \times 10^1$ | 81 | 75 | 77 | 78 | $3.84 \times 10^{-2}$ |
| 12 | $10^2$ | 137 | 140 | 154 | 144 | $1.42 \times 10^{-2}$ |

TABLE 5

Toxicity of compound 3

| Conditions | t(min) | Aliquot dilution | Colony Counts | | | Average count | N/No |
|---|---|---|---|---|---|---|---|
| NO x-ray | 0 | $10^\circ$ | 87 | 93 | 78 | 86 | 1 |
| | 30 | $10^\circ$ | 97 | 69 | 76 | 81 | $9.38 \times 10^{-1}$ |
| | 60 | $10^\circ$ | 84 | 120 | 87 | 97 | $1.13 \times 10^\circ$ |
| NO x-ray | 0 | $10^\circ$ | 124 | 139 | 133 | 132 | 1 |
| | 30 | $10^\circ$ | 139 | 143 | 155 | 146 | $1.10 \times 10^\circ$ |
| | 60 | $10^\circ$ | 133 | 109 | 139 | 127 | $9.62 \times 10^{-1}$ |
| | 90 | $10^\circ$ | 133 | 125 | 131 | 130 | $9.82 \times 10^{-1}$ |
| $N_2$ + x-ray | 0 | $10^\circ$ | 111 | 120 | 137 | 123 | 1 |
| | 30 | $10^\circ$ | 114 | 137 | 115 | 122 | $9.92 \times 10^{-1}$ |
| | 60 | $10^\circ$ | 146 | 133 | 135 | 138 | $1.12 \times 10^\circ$ |
| | 90 | $10^\circ$ | 117 | 157 | 118 | 131 | $1.06 \times 10^\circ$ |
| $O_2$ + x-ray | 0 | $10^\circ$ | 96 | 77 | 59 | 77 | 1 |
| | 20 | $10^\circ$ | 82 | 79 | 97 | 86 | $1.12 \times 10^\circ$ |
| | 40 | $10^\circ$ | 100 | 93 | 92 | 95 | $1.23 \times 10^\circ$ |
| | 60 | $10^\circ$ | 88 | 97 | 98 | 94 | $1.22 \times 10^\circ$ |

TABLE 6

X-ray sensitisation of compound 3 under hypoxic conditions

| Dose | Dilution | Colony counts | | | Average Count | N/No |
|---|---|---|---|---|---|---|
| 0 | $10^\circ$ | 110 | 102 | 105 | 106 | 1 |
| 3 | $5 \times 10^\circ$ | 158 | 167 | 169 | 165 | $3.11 \times 10^{-1}$ |
| 3.5 | $10^1$ | 109 | 111 | 106 | 109 | $1.02 \times 10^{-1}$ |
| 4 | $10^1$ | 28 | 37 | 30 | 32 | $2.99 \times 10^{-2}$ |
| | $10^2$ | 110 | 115 | 142 | 122 | $1.15 \times 10^{-2}$ |
| 0 | $10^\circ$ | 56 | 65 | 74 | 65 | 1 |
| 3 | $5 \times 10^\circ$ | 36 | 44 | 29 | 36 | $1.12 \times 10^{-1}$ |
| 5 | $10^3$ | 80 | 71 | 73 | 75 | $1.15 \times 10^{-1}$ |
| 0 | $10^\circ$ | 99 | 76 | 80 | 85 | 1 |
| 2 | $2 \times 10^\circ$ | 75 | 85 | 91 | 84 | $4.92 \times 10^{-1}$ |
| 3 | $5 \times 10^\circ$ | 26 | 28 | 24 | 26 | $6.12 \times 10^{-2}$* |
| 4 | $2 \times 10^1$ | 7 | 2 | 5 | 5 | $2.74 \times 10^{-3}$* |
| 5 | $5 \times 10^2$ | 28 | 24 | 30 | 27 | $6.43 \times 10^{-4}$ |

| Dose | Dilution | Colony counts | | | Average Count | N/No |
|---|---|---|---|---|---|---|
| 0 | $10^\circ$ | 60 | 61 | 54 | 58 | 1 |
| 2 | $2 \times 10^\circ$ | 78 | 72 | 74 | 75 | $6.44 \times 10^{-1}$ |
| 3 | $2 \times 10^\circ$ | 17 | 30 | 45 | 31 | $2.64 \times 10^{-1}$ |
| 3.5 | $2 \times 10^1$ | 30 | 55 | 43 | 43 | $3.68 \times 10^{-2}$ |
| 4.0 | $10^2$ | 19 | 32 | 19 | 23 | $4.02 \times 10^{-3}$ |
| 4.5 | $5 \times 10^2$ | 21 | 26 | 31 | 26 | $8.97 \times 10^{-4}$ |
| 5.0 | $10^3$ | 28 | 29 | 26 | 28 | $4.77 \times 10^{-4}$ |
| 5.5 | $10^3$ | 4 | 18 | 19 | 14 | $2.36 \times 10^{-4}$* |
| 0 | $10^\circ$ | 55 | 54 | 50 | 53 | 1 |
| 1.5 | $10^\circ$ | 40 | 38 | 49 | 42 | $7.99 \times 10^{-1}$ |
| 2.5 | $2 \times 10^\circ$ | 23 | 30 | 24 | 26 | $2.42 \times 10^{-1}$ |
| 3.0 | $2 \times 10^\circ$ | 7 | 3 | 3 | 4 | $4.02 \times 10^{-2}$* |
| 4.0 | $1 \times 10^2$ | 7 | 12 | 8 | 9 | $1.7 \times 10^{-3}$* |
| 5 | $5 \times 10^2$ | 7 | 15 | 5 | 9 | $3.40 \times 10^{-4}$* |
| 0 | $10^\circ$ | 71 | 66 | 73 | 70 | 1 |
| 2.5 | $2 \times 10^\circ$ | 47 | 34 | 42 | 41 | $2.93 \times 10^{-1}$ |
| 3.0 | $2 \times 10^1$ | 43 | 49 | 40 | 44 | $3.14 \times 10^{-2}$ |
| 3.5 | $1 \times 10^2$ | 38 | 39 | 32 | 36 | $5.19 \times 10^{-3}$ |
| 4 | $2 \times 10^2$ | 24 | 44 | 42 | 37 | $2.62 \times 10^{-3}$ |
| 4 | $1 \times 10^3$ | 111 | 161 | 117 | 130 | $1.85 \times 10^{-3}$ |

TABLE 7

X-ray sensitisation of compound 3 under oxic conditions

| Dose | Dilution | Colony counts | | | Average Count | N/No |
|---|---|---|---|---|---|---|
| 0 | $10^0$ | 48 | 46 | 50 | 48 | 1 |
| 3 | $2 \times 10^0$ | 45 | 51 | 43 | 46 | $4.83 \times 10^{-1}$ |
| 6 | $10^1$ | 113 | 125 | 110 | 116 | $2.42 \times 10^{-1}$ |
| 10 | $5 \times 10^1$ | 114 | 132 | 142 | 129 | $5.39 \times 10^{-2}$ |
| 12 | $10^2$ | 122 | 142 | 132 | 132 | $2.75 \times 10^{-2}$ |
| 0 | $10^0$ | 55 | 73 | 45 | 58 | 1 |
| 4 | $5 \times 10^0$ | 75 | 82 | 79 | 79 | $2.71 \times 10^{-1}$ |
| 8 | $2 \times 10^1$ | 93 | 76 | 79 | 76 | $6.55 \times 10^{-2}$ |
| 14 | $2 \times 10^2$ | 68 | 78 | 77 | 74 | $6.41 \times 10^{-3}$ |
| 16 | $5 \times 10$ | 85 | 86 | 79 | 83 | $2.87 \times 10^{-3}$ |

We claim:

1. A pharmaceutical composition comprising an effective amount of a coordination compound having the general empirical formula $$[Rh^{III}X_xY_y]^a$$

in which X is at least one anionic ligand, Y is at least one neutral ligand, with the proviso that at least one of X and Y is a nitrogen donor ligand, x is an integer from 1 to 6, y is an integer from 1 to 5 or may be equal to zero, and a is a positive or negative integer from $-3$ to $+3$ or may be equal to zero, in association with a pharmaceutically-acceptable carrier, diluent or excipient therefor.

2. A composition according to claim 1, in which the anionic ligand X is selected from the group consisting of nitrite, halogen, hydroxy, azide, thiocyanate, formate, acetate, chloroacetate, carbonate, oxalate, malonate, sulphate, thiosulphate and aminoacid.

3. A composition according to claim 1, in which the neutral ligand Y is a monodentate ligand selected from the group consisting of ammine, pyridine and water or a bidentate ligand selected from the group consisting of ethylenediamine, ethylenediaminetetraacetic acid and dimethylglyoxime.

4. A composition according to claim 1, in which the formula of the compound is $[RhenCl_4]_2[enH_2]$.

* * * * *